US006679260B2

United States Patent
Her

(10) Patent No.: US 6,679,260 B2
(45) Date of Patent: Jan. 20, 2004

(54) APPARATUS AND METHOD FOR FORMING A VENTILATION MASK

(76) Inventor: Ching-Ling Her, No. 81, Lane 98, Li-Der Street, Chung-Ho City, Taipei County (TW)

( * ) Notice: Subject to any disclaimer, the term of this patent is extended or adjusted under 35 U.S.C. 154(b) by 143 days.

(21) Appl. No.: 09/768,610

(22) Filed: Jan. 25, 2001

(65) Prior Publication Data

US 2002/0096175 A1 Jul. 25, 2002

(51) Int. Cl.⁷ .............................................. A62B 18/08
(52) U.S. Cl. ........................ 128/206.26; 128/206.21; 128/206.24
(58) Field of Search ................. 128/206.26, 206.24, 128/206.12, 206.21

(56) References Cited

U.S. PATENT DOCUMENTS

| | | | | |
|---|---|---|---|---|
| 1,410,928 A | * | 3/1922 | Knoblock | 128/206.16 |
| 1,960,544 A | * | 5/1934 | Malcom | 128/201.15 |
| 2,254,854 A | * | 9/1941 | O'Connell | 128/206.26 |
| 2,540,567 A | * | 2/1951 | Bennett | 128/206.26 |
| 2,666,432 A | * | 1/1954 | Stanton | 128/206.26 |
| 2,875,757 A | * | 3/1959 | Galleher, Jr. | 128/206.26 |
| 3,330,274 A | * | 7/1967 | Bennett | 128/206.26 |
| 4,337,767 A | * | 7/1982 | Yahata | 128/206.26 |
| 4,799,477 A | * | 1/1989 | Lewis | 128/200.27 |
| 4,807,617 A | * | 2/1989 | Nesti | 128/203.29 |
| 4,811,730 A | * | 3/1989 | Milano | 128/202.28 |
| 4,905,686 A | * | 3/1990 | Adams | 128/204.17 |
| 4,971,051 A | * | 11/1990 | Toffolon | 128/206.26 |
| 5,146,914 A | * | 9/1992 | Sturrock | 128/202.29 |
| 5,220,699 A | * | 6/1993 | Farris | 128/200.24 |
| 5,355,879 A | * | 10/1994 | Brain | 128/207.14 |
| 5,429,683 A | * | 7/1995 | Le Mitouard | 128/205.25 |
| 5,647,357 A | * | 7/1997 | Barnett et al. | 128/205.25 |
| 5,724,965 A | * | 3/1998 | Handke et al. | 128/205.25 |
| 5,738,094 A | * | 4/1998 | Hoftman | 128/206.24 |
| 5,975,079 A | * | 11/1999 | Hellings et al. | 128/206.21 |
| 6,035,852 A | * | 3/2000 | Hoftman | 128/206.21 |

* cited by examiner

Primary Examiner—Weilun Lo
Assistant Examiner—Mital Patel
(74) Attorney, Agent, or Firm—Bacon & Thomas, PLLC

(57) ABSTRACT

An apparatus and method for a ventilation mask. The ventilation mask includes an upper hood and a toroidal tube. The toroidal tube is made of soft silicone, and a tube shape is first formed when the middle part of the tube shape is formed into an "S" shape, and whenever the lower part of the "S" is turned upwardly and inwardly, the "S" part will form the toroidal tube. Air can be injected into the toroidal tube so as to conform the face of the patient. An assembly member is used to assemble the upper hood and the toroidal tube. The advantages of the ventilation mask include added comfort, excellent air tightness, transparency. The toroidal tube can be disassembled to be disinfected for repeated use or for replacement. The upper hood does not have to be replaced.

6 Claims, 5 Drawing Sheets

APPARATUS AND METHOD FOR FORMING A VENTILATION MASK

FIELD OF THE INVENTION

The present invention relates to an improvement of a ventilation mask, and more particularly to a structure design of a low cost ventilation mask that can conform to a patient's face, and can be disassembled to disinfect for repeated use.

BACKGROUND OF THE INVENTION

A ventilation mask is used for covering a patient's mouth and nose to deliver oxygen or anesthetic. Two types of popular ventilation mask are described, as below:

The first type of ventilation mask 10 is shown in FIG. 1, an upper hood 11 is made of hard polycabonate or polysulfone, and is provided with a connecting tube 111 for delivering oxygen. A lower part 12 is made of soft silicone, with the end thereof being bent for covering the mouth and nose of a patient. Since everyone's face are different, the fixed shape of the lower part 12 actually cannot conform to everyone's face, so oxygen is very easy to leak out. The silicone material of the lower part 12 has several advantages, such as having fixed shape, and being transparent for observing the breath of the patient, so it is very expensive, and is very hard for the hospital to discard very often. However, the repeated use of the first type of ventilation mask will cause infectious diseases to be spread between patients, so American countries often refuse to use the first type of ventilation mask.

The second type of ventilation mask is shown in FIG. 2, and is made integrally of PVC material. An upper hood 21 uses hard PVC, and is provided with a connecting tube 211 for delivering oxygen, a lower part is formed into a toroidal tube 22 by soft PVC material to be bound with the upper hood 21. Air is injected into the toroidal tube 22 through the connecting tube 221 so that the toroidal tube 22 can conform to the face of the patient. This type of ventilation mask is better than the first type, the oxygen entered into the upper hood 21 will not leak out very easily. Since the PVC material is not expensive, the cost is therefore reduced. However, this type of ventilation mask can't be disinfected in high temperature, and have to be discarded after use, therefore causes some environmental problems of too much garbage.

SUMMARY OF THE INVENTION

It is therefore an object of the present invention to provide an improvement for the ventilation mask, comprising an upper hood and a toroidal tube. The toroidal tube is made of soft silicone by first forming a tube type, the middle part of the tube type is formed into an "S" shape, whenever the lower part of the "S" is turned upwardly and inwardly, the "S" part will form the toroidal tube. Air can be injected into the toroidal tube so as to conform the face of the patient. The toroidal tube is bound to the upper hood with an assembly member.

The advantages of the ventilation mask according to the present invention are being comfortable, excellent air tightness, transparency. And the toroidal tube can be disassembled to disinfect for repeated use or for replacement. The upper hood does not have to be replaced, so the garbage is reduced.

DETAILED DESCRIPTION OF THE INVENTION

Figure 1:
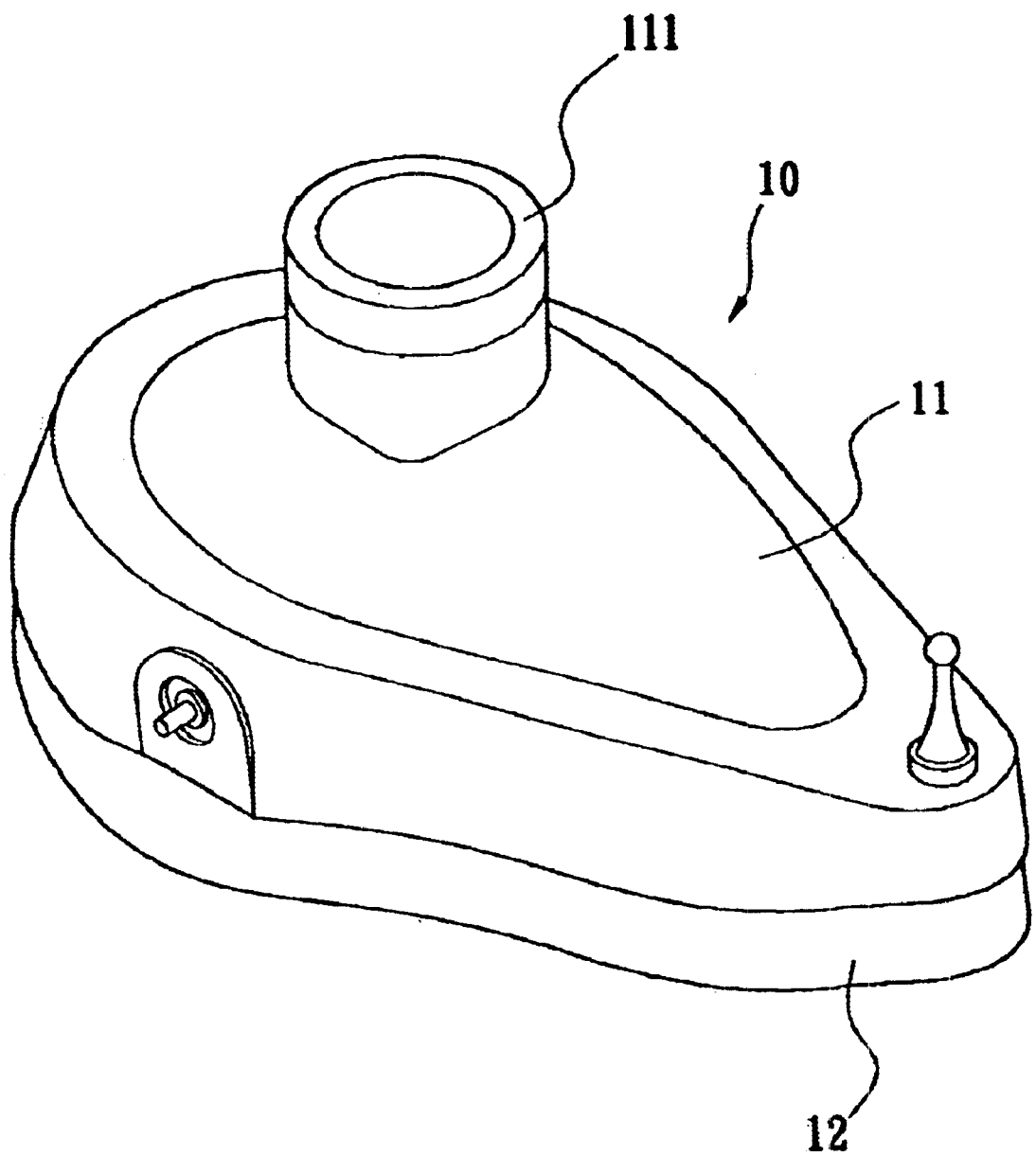
FIG. 1 shows schematically the perspective view of the first type of the conventional ventilation mask.
Figure 2:
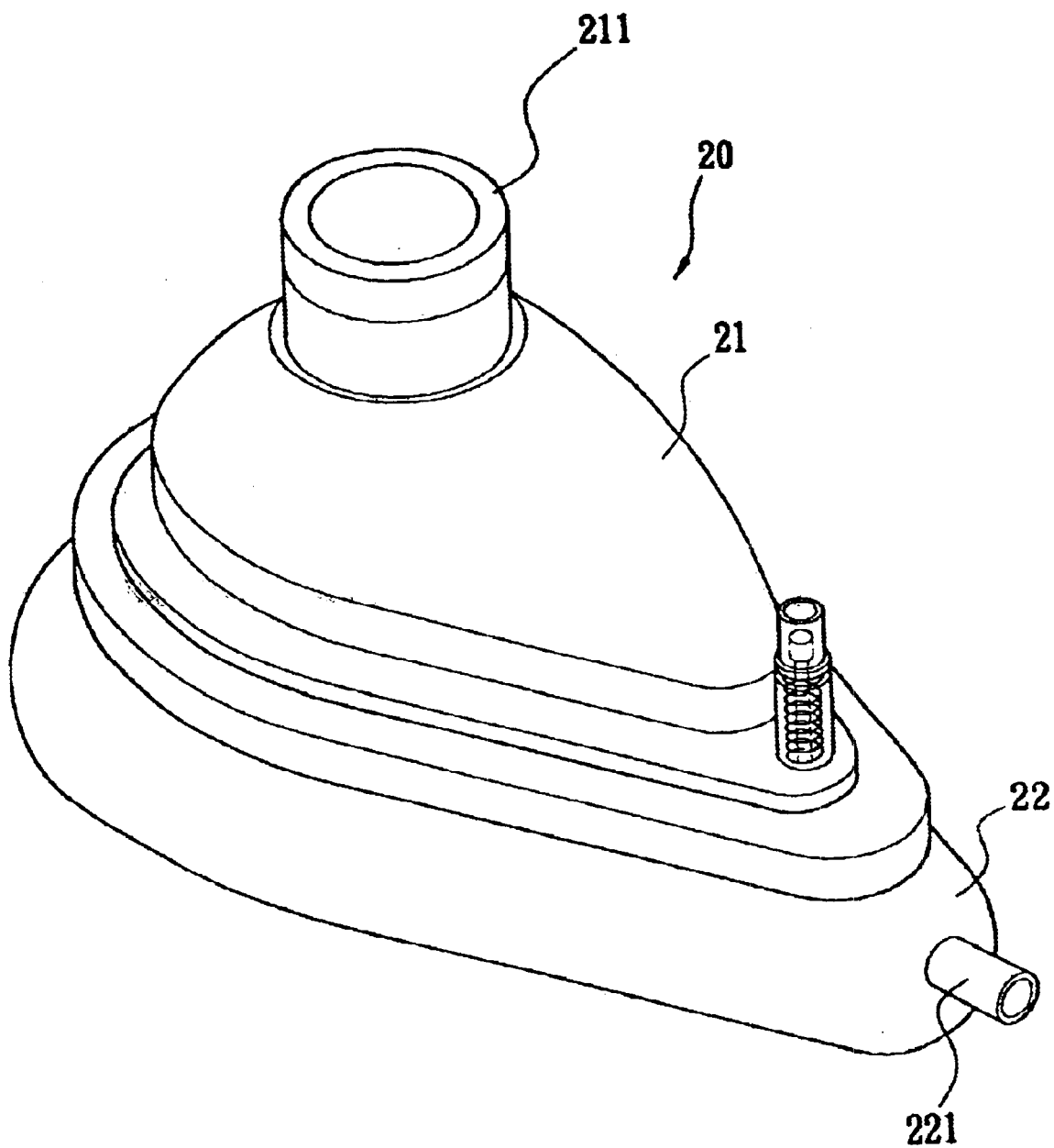
FIG. 2 shows schematically the perspective view of the second type of the conventional ventilation mask.
Figure 3:
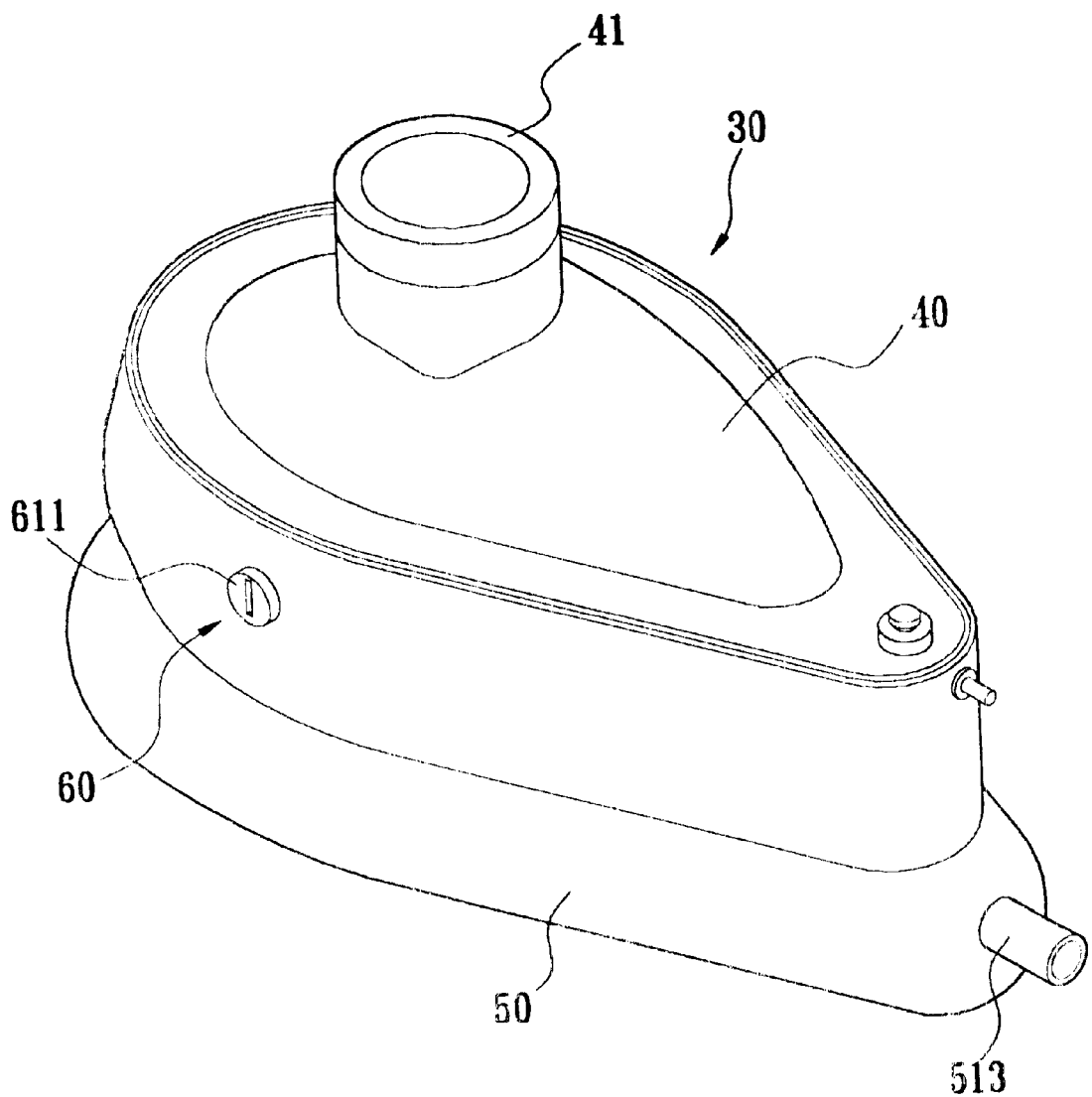
FIG. 3 shows schematically the perspective view of the ventilation mask according to the present invention.
Figure 4:
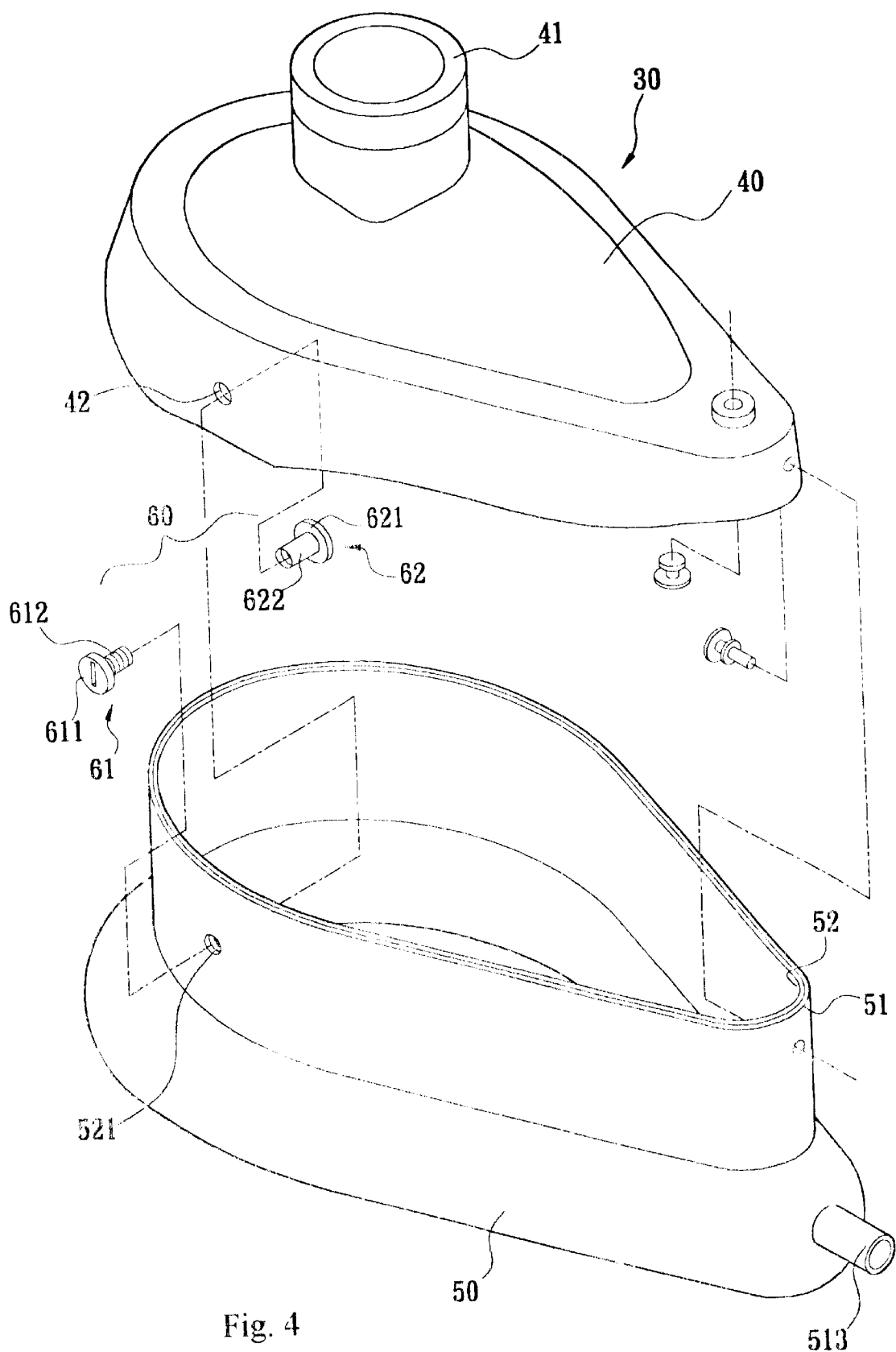
FIG. 4 shows the exploded view of the ventilation mask according to the present invention.

As shown in FIGS. 3 and 4, the ventilation mask 30 according to the present invention comprises:

an upper hood 40 made of hard polycarbonate or polysulfone, having an excellent transparency and can be disinfected in high temperature for repeated use, a connecting tube 41 being provided thereof for input of oxygen, and several punctures 42 being provided suitably along the lower periphery thereof.

Figure 5:
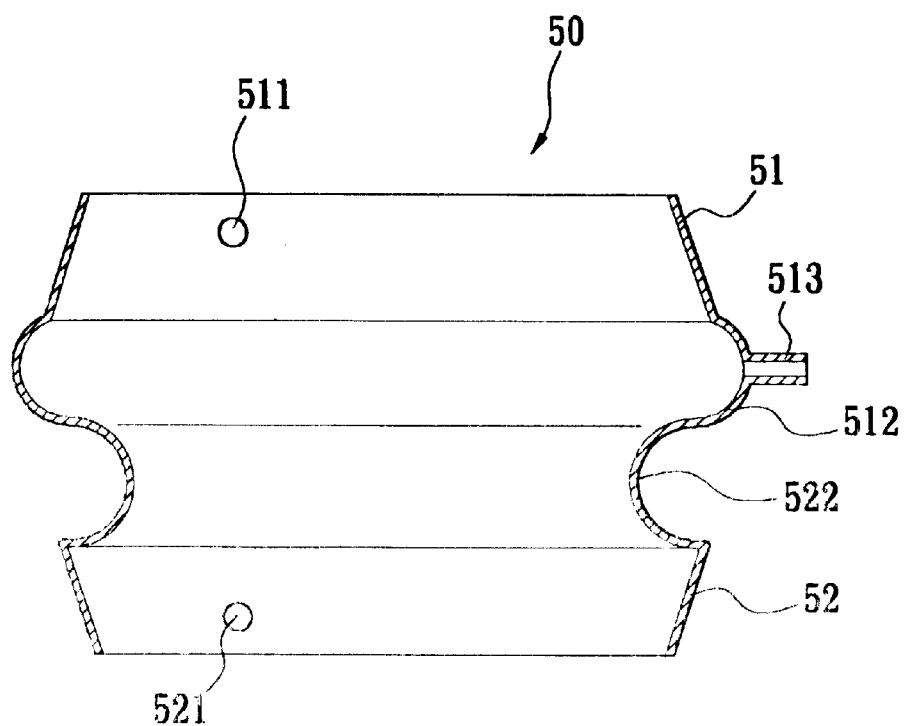
FIG. 5 shows schematically that a tube type is formed first, the middle part of the tube is formed into an "S" shape.
Figure 6:
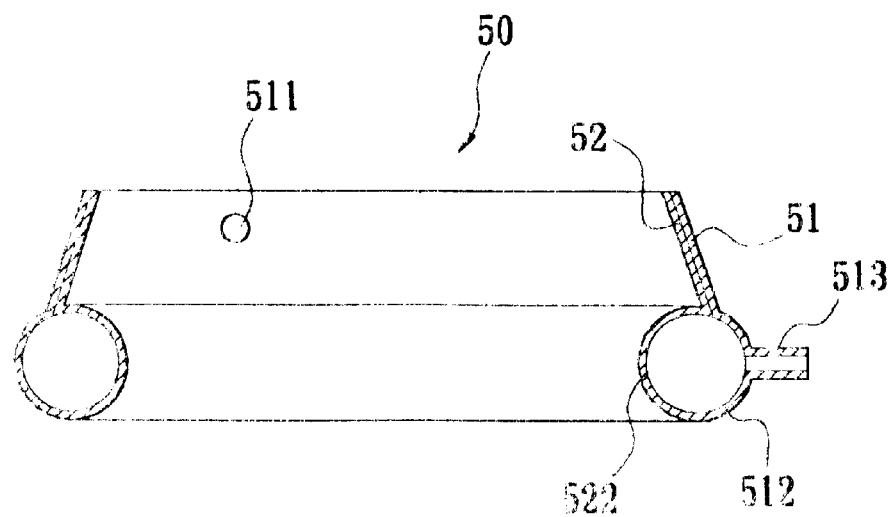
FIG. 6 shows schematically that a toroidal tube is formed with the tube type FIG. 5.

A toroidal tube 50 is made of soft silicone, and forms a tube shape (see FIG. 5), the middle part of the tube is formed into an "S" shape, and whenever the lower part of the "S" is turned upwardly and inwardly, the "S" part will form the toroidal tube 50 (see FIG. 6). The toroidal tube 50 can be injected with air, so as to conform the face of the patient.

The upper part 51 and the lower part 52 of the tube type are provided with punctures 511, 521 respectively. After the upper part 51 and the lower part 52 are attached and bound together, an assembly member 60 is used to penetrate through the puncture 42 of the upper hood 40 and the punctures 511, 521 on the upper part 51 and the lower part 52 of the tube type, therefore to form a ventilation mask 30.

A connecting tube 513 is provided suitably at the "S" part 512, 522 for injecting air into the toroidal tube 50, so that the toroidal tube 50 can conform to the face of the patient.

The assembly member 60 is used to combine the toroidal tube 50 and the upper hood 40 to form the ventilation mask 30. As shown in FIG. 4, the assembly member 60 is a button type, comprising a male button 61 and a female button 62. Each of the male button 61 and the female button 62 has a round surface 611, 621 respectively. A round pillar 612 and a round cylinder 622 are each provided at the center of the round surfaces 611, 621 respectively. When the round cylinder 622 penetrates through the puncture 42 of the upper hood 40 and the punctures 511, 521 on the upper part 51 and the lower part 52 of the tube type, and then the round pillar 612 of the male button 61 is plugged into the round cylinder 622, the ventilation mask 30 is therefore suitably assembled.

The round pillar 612 and the round cylinder 622 can be designed with screw thread, and the round surface 611 has a groove. When we loosen the assembly member 60 to separate the upper hood 40 and the toroidal tube 50, the toroidal tube 50 can be replaced or be disinfected for repeated use.

The specification above provides appropriate antecedents for a method for forming the ventilation mask.

The advantages of the ventilation mask according to the present invention are being comfortable, excellent air tightness, and transparency. And the toroidal tube can be disassembled to disinfect for repeated use or for replacement. The upper hood does not have to be replaced, so the garbage is reduced.

The scope of the present invention depends only upon the following claims, and is not limited by the above embodiment.

What is claimed is:

1. A method for forming a ventilation mask, comprising the steps of:

providing a hood having a first connecting tube provided therein for input of air, and a plurality of first punctures along a lower periphery thereof;

providing a toroidal tube, wherein the toroidal tube is made by providing a tubular shape having upper and lower parts and an S-shape cross section therebetween, a second connecting tube extending through the S-shape cross section, a plurality of second punctures on the upper and lower parts of the tubular shape, and inverting the tubular shape so that the toroidal tube is formed, wherein the upper and lower parts of the tubular shape form a double wall structure with the second punctures of the upper and lower parts of the tubular shape being superimposed on the double wall structure of the toroidal tube;

placing the lower periphery of the hood along the double wall structure so that the first punctures and the second punctures are aligned respectively; and binding the toroidal tube to the hood with assembly members that interlock through the first and second punctures respectively.

2. The method for forming a ventilation mask as claimed in claim 1, further comprising the step of injecting air through the second connecting tube so that the shape of the toroidal tube conforms to the face of a user.

3. The method for forming a ventilation mask as claimed in claim 1, wherein the hood is comprised of hard polycarbonate and the toroidal tube is comprised of soft silicone.

4. The method for forming a ventilation mask as claimed in claim 1, wherein the hood is comprised of polysulfone and the toroidal tube is comprised of soft silicone.

5. The method for forming a ventilation mask as claimed in claim 1, wherein each of the assembly members comprises a male button and a female button that detachably extend through respective ones of the first and second punctures and interlock the hood to the toroidal tube.

6. The method for forming a ventilation mask as claimed in claim 5, wherein the male and female buttons include flattened head portions having round surfaces that secure the hood to the toroidal tube.

* * * * *